United States Patent [19]

Carbrey et al.

[11] Patent Number: 5,451,795
[45] Date of Patent: Sep. 19, 1995

[54] APPARATUS FOR SPOTTING LABELS ONTO A SURFACE HAVING A TRANSPARENT CONVEYOR MEANS

[75] Inventors: Robert J. Carbrey, North Wales, Pa.; Halvard H. Solberg, Titusville, N.J.; John DiValerio, Havertown, Pa.

[73] Assignee: Crathern & Smith, Inc., Huntingdon Valley, Pa.

[21] Appl. No.: 234,268

[22] Filed: Apr. 28, 1994

[51] Int. Cl.[6] ............................................. G01N 21/86
[52] U.S. Cl. ............................. 250/556.29; 250/223 R
[58] Field of Search ...................... 250/561, 559, , 571, 250/208.1, 221, 222.1, 223 R, 223 B; 356/400; 348/88, 94, 95; 198/811, 841, 860.1

[56] References Cited

U.S. PATENT DOCUMENTS

| | | | |
|---|---|---|---|
| 3,778,618 | 12/1973 | Laskowsi et al. | 250/223 |
| 4,074,130 | 2/1978 | Messman et al. | 250/223 R |
| 4,682,023 | 7/1987 | Yoshida | 250/223 B |
| 4,750,035 | 6/1988 | Chang et al. | 358/106 |
| 4,929,843 | 5/1990 | Chmielewski et al. | 250/561 |
| 4,943,713 | 7/1990 | Yoshida | 250/223 B |
| 5,013,927 | 5/1991 | Tsikos et al. | 250/561 |
| 5,095,204 | 3/1992 | Novini | 250/223 B |
| 5,216,239 | 6/1993 | Yoshida | 250/223 B |
| 5,220,177 | 6/1993 | Harris | 250/561 |
| 5,245,399 | 9/1993 | Wertz et al. | 250/226 |

*Primary Examiner*—David C. Nelms
*Assistant Examiner*—John R. Lee
*Attorney, Agent, or Firm*—Lappin & Kusmer

[57] ABSTRACT

A system for registering boxes carried on one conveyor line with wraps carried on another conveyor line, in which the boxes and wraps are viewed by electronic cameras that provide respective digitized images of the boxes and wraps, and a computer determines from those images sufficient information to effect such registration by a mechanical arm that spots the boxes on the wraps regardless of their original orientation, responsively to commands from the computer. A vacuum plenum is disposed beneath the wrap conveyor for maintaining a negative pressure that releasably retains the wraps on a surface of the wrap conveyor. The wrap conveyor comprises a flexible, pneumatically porous, light-transmissive conveyor belt for moving the wraps for viewing by a camera against the upper surface of the belt, the belt being supported over the vacuum plenum on an apertured, light-transmissive frame. A diffuse light source is also provided for lighting the opposite surface of the belt so as increase the optical contrast between the wraps and the upper surface of the belt.

8 Claims, 1 Drawing Sheet

APPARATUS FOR SPOTTING LABELS ONTO A SURFACE HAVING A TRANSPARENT CONVEYOR MEANS

This invention relates to spotting or registration apparatus and more particularly to an automatic optical system for applying labels to a surface.

BACKGROUND OF THE INVENTION

Spotting equipment generally can be considered to be apparatus that matches sequentially presented items to a corresponding sequence of other items in a predetermined geometrical relationship with one another, i.e. registration. For example, spotting apparatus is useful in matching labels to boxes or applying flexible wrappings (i.e. wraps) to containers or boards, and the like. The terms "label" and "wrap" as used herein, sometime interchangeably, is not intended to be limited to a sheet or notice or that is inscribed or printed with information or a pattern, but in a broader sense, simply identifies a sheet of material that may have any particularly desired flexibility or stiffness, so as to include board wrappings and the like.

There are a number of prior art systems that examine objects such as containers or labels optically for a number of purposes, that can be used to automatically register labels with corresponding containers and spot the properly registered label on a surface of the box or vice-versa. For example, U.S. Pat. No. 3,778,618 (Laskowski) shows an apparatus for detection of transparent or translucent sheets passing on a conveyor wherein an opaque flap is disposed so as to be movable by the leading edge of a sheet as the latter is carried by a light transmissive conveyor belt into the path of light and detected by a photosensor, thereby identifying the position of that leading edge. The release of the flap from the trailing edge of the sheet results in detection of the position of the trailing edge by the photosensor. Because the system only detects the positions of those pans of the leading and trailing edges engaged with the flap, the information obtained is highly limited. Thus, where the leading and trailing edges of the sheet are not normal to the direction of travel of the conveyor, or the sheets are randomly oriented on the conveyor, the information obtained by the photodetector is necessarily incomplete, ambiguous and will not serve adequately to provide precise registration based on that information.

U.S. Pat. No. 4,750,035 (Chang et al.) discloses apparatus for video inspection of containers to determine quality, cleanliness and the like, wherein light is projected through transparent or translucent containers moving on a conveyor and captured on CCD video cameras to provide multiple views of the entire expanse of the sides of the containers from different angularly spaced positions. The different views of the same container are then compared with one another, a data processor correlates the images to analyze for defect patterns and defective containers are rejected.

U.S. Pat. Nos. 4,682,023 (Yoshida), 4,943,713 (Yoshida), 5,216,239 (Yoshida) and 5,095,204 (Novini) are of interest as showing inspection means using light and a light-sensitive element such as a photosensor or video camera to detect defects in the bottoms of light transmissive containers.

Information for registration can be predetermined by nesting the wrap and/or the object in preformed cavities or nests in or on the conveyor belt, but such nests necessarily limit the system to specific forms and sizes of wrap and object and the system therefore lacks flexibility of use. Further, such nesting would not ordinarily provide any information as to misfit items that may fit the nest poorly or are incorrectly oriented.

To effect reasonably adequate registration, for example between a wrap or label and an object such as a box, requires detailed knowledge of the size, shape and orientation in at least two dimensions of the wrap and object. Such information with respect to the wrap and object can readily be provided by optical viewing means such as electronic camera means that view the wrap and/or object being carried on conveyor means and provide digitized images suitable for processing in a digital computer as in the prior art. However, whether or not the prior art equipment uses a single camera or two cameras, it suffers from a number of problems, particularly where one wishes to provide adequate data, not only for inspection, but to provide reasonably precise registration between, for example, a label and a box. Although data as to size, shape and orientation can often be obtained from determination of the outlines of the label and box as by cameras, if the conveyor surfaces on which the labels and boxes are carried do not contrast sufficiently with the latter, the information provided either to the camera or to a computer processing the camera output may be inadequate or incomplete. For example, even the use of high intensity illumination reflected from the label and surface of the conveyor belt may not prove efficacious if the color and albedo of the label and the conveyor belt are very close, because the signal-to-noise ratio will tend to be very poor.

A principal object of the present invention is therefor to provide a spotting system that overcomes the above-identified problems of the prior art. Yet other objects of the present invention are to provide such as system in which the signals generated by a camera viewing a conveying surface and items supported thereon are optimized; to provide such a system in which such optimization is effected by increasing the optical contrast between the conveyor surface and an item carried thereon so that the signal-to-noise ratio of signals provided by the camera is increased; and to provide such a system that is relatively inexpensive and is capable of high speed operation.

SUMMARY OF THE INVENTION

To effect the foregoing and other objects, the present invention generally is an improved apparatus for matching sequentially presented items of a first group such as a set of labels, to a corresponding sequence of other items of a second group such as a set of boxes, in registration with one another. The apparatus comprises electronic video means comprising one or more cameras for forming respective digitized images of a sequentially presented labels and sequentially presented box as carried on conveyor means. Computer means are provided for determining from the digitized images if the respective label and box meet predetermined quality criterior as to dimension, shape and orientation, and determines whether the label and box are matched for each other. Pick-up means are provided for physically spotting the label on the box or vice-versa in proper registration regardless of their original orientation, responsively to the computer determination.

An important aspect of the present invention is the provision of the conveyor means in the form of at least one pneumatically porous, light-transmissive conveyor belt for moving the labels on one surface thereof in sequence though the focal plane of a camera, the belt being supported on an apertured, light transmissive frame over a vacuum plenum in which a negative pressure is maintained to releasably retain the labels on the belt. Means are provided for illuminating the other surface of the belt so as to backlight the labels, preferably diffusely, and provide a high contrast between the label and belt as viewed by the camera.

BRIEF DESCRIPTION OF THE DRAWING

For a fuller understanding of the nature and objects of the present invention, reference should be had to the following detailed description taken in connection with the accompanying drawing which is a schematic diagram, partly cut-away, illustrating apparatus embodying the principles of the present invention.

DETAILED DESCRIPTION OF THE DRAWINGS

Figure 1:
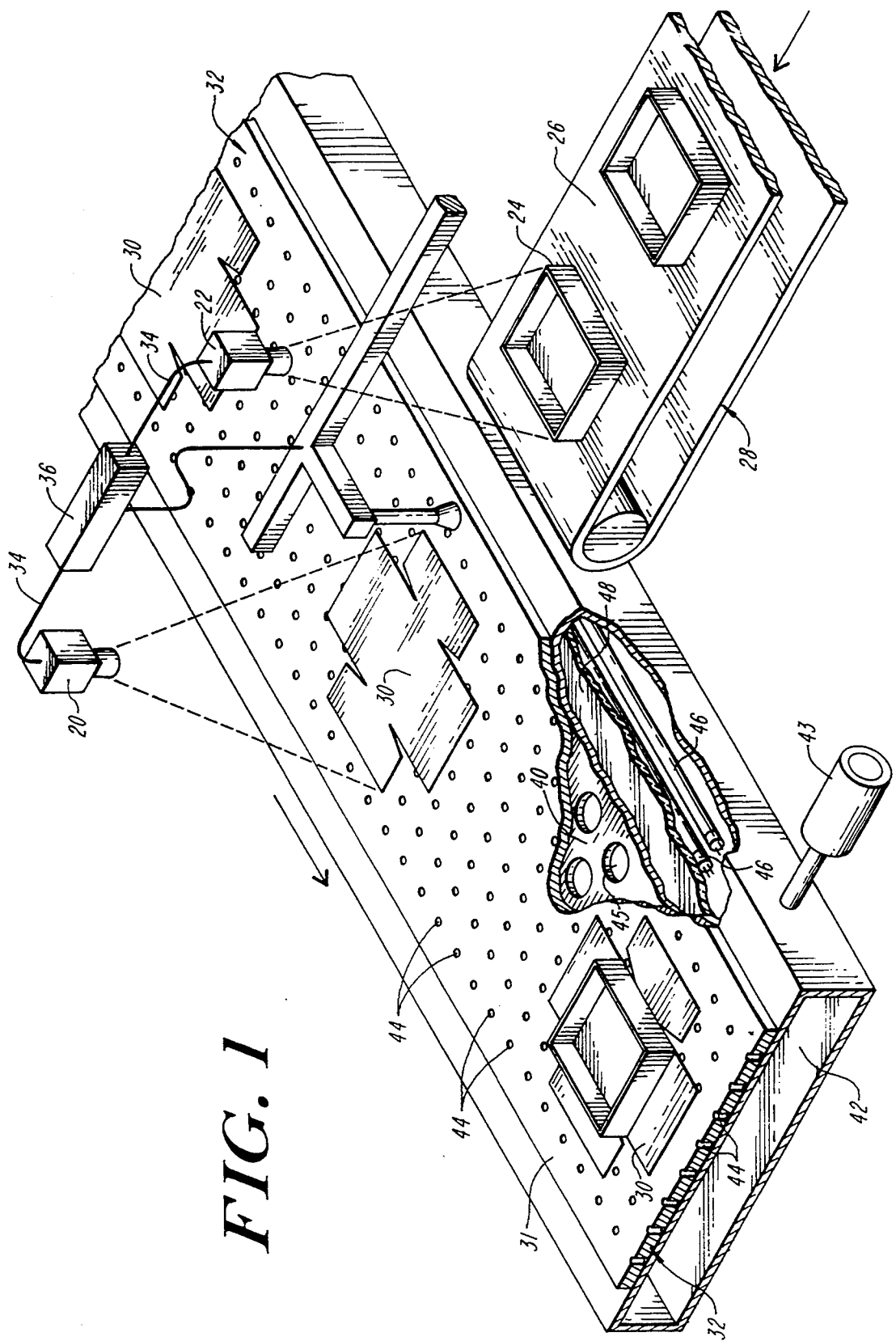

As shown in the drawing, a preferred embodiment of the present invention comprises electronic camera means typically formed of a pair of well-known charge-coupled device (CCD) video cameras 20 and 22 such as the commercially available Sony model XC-77 monochrome CCD camera. Camera 22 is disposed for viewing box 24 (typically made of paper, metal, plastic and the like), preferably as a top view, against the background of a supporting surface 26 of conveyor means comprising flexible conveyor belt 28 which is intended to move a sequence of such boxes. CCD camera 20 similarly is disposed for sequentially viewing wraps 30 (e.g. formed as relatively flat sheets of paper, plastic, metal foil and the like) against the background of a supporting surface 31 of conveyor means comprising conveyor belt 32 which is intended to move a sequence of such wraps which may be randomly oriented on the belt. CCD camera 20, in operation, provides electronic signals equivalent to digitized images of successive wraps 30 and camera 22 similarly provides signals with respect images of boxes 24 as they are successively provided by conveyor belt 28. Such signals preferably include data as to size, shape and orientation of each viewed or photographed wrap and box with respect to a fixed frame of reference against the background of the supporting surfaces of the conveyor belts.

Means are provided in the form of leads 34 for feeding the digitized image signals from the cameras to electronic computer 36 that is preferably programmed in known manner to determine if the respective box and wrap identified by each sequence of signals meet predetermined quality criteria as to dimensions, shape and orientation, to determine whether the box and wrap are matched for each other, and to provide commands to effect spotting of a box on a corresponding wrap. It will be appreciated that computer 36 can be a general purpose digital computer, a dedicated digital computer or even analog computer or hardwired circuit. Means, in the form of movable arm 38 mechanism operable responsively to computer commands from computer 36 based on the digitized information from the cameras, are positioned to pick up computer-approved ones of boxes 24 and spot them on corresponding computer-approved wraps 30 regardless of the original orientation of that box and wrap. The pick up of the boxes by mechanism of arm 38 may be achieved by vacuum, adhesion, magnet field or the like (depending on the nature of the box material). At least belt 32 is provided as a flexible mesh or pneumatically porous belt, mounted for sliding movement on the upper surface of supporting frame 40 over vacuum plenum 42 in which a negative pressure is maintained by pump 43 to releasably retain the flat wraps 30 in relatively fixed, but releasable positions on the belt. To this end, belt 32 typically can be provided with a plurality of apertures 44, typically around $\frac{1}{8}$ to $\frac{1}{4}''$ in diameter, extending between the opposed longitudinal surfaces of the belt so as to serve as pneumatically communicating passageways between the atmospheric pressure at the outer surface 31 of belt 32 and the reduced pressure in vacuum plenum 42. Similarly, frame 40 is also provided as an open network or grid, and, for example, is formed of a sheet of substantially rigid material having a plurality of large apertures or holes 45, e.g. $\frac{1}{2}''$ in diameter, therein through which gas can pass between plenum 42 and apertures 44. Belt 28 can be formed similarly to belt 32 but if the boxes or other objects conveyed on it are relatively heavy enough to tend to remain in a fixed position at least during viewing by camera 22, belt 28 need not be porous, and a corresponding vacuum plenum need not be provided.

So that a substantial optical contrast between wrap 30 and surface 31 will be provided by the present invention, porous conveyor belt 32 is formed of light-transmissive (i.e. either translucent or transparent) material such as a flexible, light-transmissive urethane reinforced with light-transmissive fibers such as glass, polyester, polystyrene, polycarbonate and the like. Similarly, because belt 32 necessarily runs across frame or grid 40 which provides both support and an open structure so that the vacuum in plenum 42 can draw air through the belt, in order to avoid or limit shadows of grid 40 on belt 32, grid 40 is formed of light-transparent or highly translucent plastic or glass material, preferably of polytetrafluorethylene or other material having a very low coefficient of friction. The slippery aspect of grid 40, while desirable, is not necessary. In combination with light-transmissive belt 32 and light-transmissive supporting grid 40 is a light source, shown as a plurality of elongated electrical lamps 46, typically fluorescent, positioned within plenum 42 so as to backlight belt 32. Disposed between lamps 46 and belt 32, preferably underlying frame 40 is optical scattering or dispersive means, typically a layer or diffuser sheet 48 of light-transmissive, frosted or opal plastic or glass.

In operation, respective sequences of boxes 24 and wraps 30 intended to be registered with and applied to the boxes are carried along respective conveyor belts 28 and 32 in the direction indicated by the arrows to where they can be viewed by respective cameras 20 and 22. Neither the spacing or orientation of the respective wraps or labels on the conveyor belts is critical because the precise location, size and orientation of the wraps and boxes are determined by cameras 20 and 22. Once the latter have viewed a respective one of the wraps and labels, the optical information regarding size, shape and orientation of the wrap and the box is digitized, fed to computer 36 and used to control the timing of the pick up of a box 24 by arm 38 and the spotting of the box in proper registration. Alternatively, if the data determined by the computer indicates that the box and wrap are mismatched beyond preset limits, or either the box or wrap is defective in failing to meet some preestablished criteria, then the mismatched or defective items are discarded. The diffuse backlighting provided by lamps 46, diffuser sheet 48 and the optical transmissivity of frame 40 all serve to provide a relatively high intensity, uniform light background or glow to the upper surface 31 of belt 32. Inasmuch as a basic aim of the present invention is to enhance the contrast between the wrap and its background, it should be kept in mind that contrast can be improved in a manner other than increasing the intensity difference of radiant emissions between the wrap and background as hereinbefore described using a camera that provides signals that are proportional to that intensity difference. In certain instances one can take advantage of the spectral sensitivity of a number of known cameras and enhance contrast by spectral difference. For example, where wraps 30 are light transmissive in a particular wave band or color, a different color can be provided to belt 32 (e.g. by changing the emission spectrum of lamps 46 or interposing a color filter between belt 32 and lamps 46 as by staining diffuser sheet 48.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. In a system for registration of items of a first set sequentially presented on movable conveyor means, to corresponding members of a sequence of a second set of presented items, including means for forming respective digitized images of items of said first set and items of said second set, a vacuum plenum disposed adjacent said conveyor means so as to maintain a negative pressure for releasably retaining said items of said first set on a surface of said conveyor means, computer means for determination of sufficient information from said digitized images to effect such registration, and means for physically spotting an item of said second set with respect to an item of said first set in said registration regardless of the original orientation of said items and responsively to said the determination by said computer means, the improvement wherein said conveyor means comprises a flexible, pneumatically porous, light-transmissive conveyor belt for moving said items of said first set for viewing by said video means against one surface of said belt, apertured frame means for supporting said belt over said vacuum plenum for movement with respect to said frame means; and means for illuminating said opposite surface of said belt so as to backlight said items of said first set against said one surface of said belt during viewing thereof by said video means.

2. The improvement as set forth in claim 1 wherein said pores of said belt are dimensioned in the range of about $\frac{1}{8}''$ to $\frac{1}{4}''$ in cross-section.

3. The improvement as set forth in claim 1 wherein said belt is formed of a fiber-reinforced plastic material.

4. The improvement as set forth in claim 1 wherein said belt is formed as a flexible mesh.

5. The improvement as set forth in claim 1 wherein said frame means is formed of a light-transmissive material.

6. The improvement as set forth in claim 5 wherein said material of said frame means has a coefficient of friction low enough to permit said belt to slide easily across said frame means.

7. The improvement as set forth in claim 1 wherein the illumination provided by said means for illuminating is diffuse.

8. The improvement as set forth in claim 7 including light source means positioned within said vacuum plenum and wherein said diffuse illumination is provided by a light-transmitting and diffusing sheet disposed between said belt and said light source means.

* * * * *